US012386345B2

(12) United States Patent
Sukkau et al.

(10) Patent No.: US 12,386,345 B2
(45) Date of Patent: Aug. 12, 2025

(54) PREDICTING A POTENTIAL FAILURE OF A MODULE FOR USE IN A MAGNETIC RESONANCE APPARATUS

(71) Applicant: Siemens Healthcare GmbH, Erlangen (DE)

(72) Inventors: Johann Sukkau, Herzogenaurach (DE); Mario Zeller, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 251 days.

(21) Appl. No.: 17/347,564

(22) Filed: Jun. 14, 2021

(65) Prior Publication Data

US 2021/0389759 A1     Dec. 16, 2021

(30) Foreign Application Priority Data

Jun. 15, 2020   (DE) .................... 10 2020 207 363.5

(51) Int. Cl.
*G05B 23/02*    (2006.01)
*A61B 5/055*    (2006.01)
*G01R 31/00*    (2006.01)
*G06N 3/044*    (2023.01)

(52) U.S. Cl.
CPC .......... *G05B 23/0283* (2013.01); *A61B 5/055* (2013.01); *G01R 31/00* (2013.01); *G06N 3/044* (2023.01)

(58) Field of Classification Search
CPC ............. G01R 33/341; G01R 33/3657; G01R 33/34084; G01R 33/3415; G01R 33/34007; G01R 33/28; G01R 33/288; G01R 33/3804; G01R 33/36; G01R 33/0035; G01R 35/005; G01R 31/00; A61B 5/055; G05B 23/0283; G06N 3/044
See application file for complete search history.

(56) References Cited

U.S. PATENT DOCUMENTS

| 5,097,252 A | 3/1992 | Harvill et al. |
| 6,127,672 A | 10/2000 | Danisch |
| 7,560,920 B1 * | 7/2009 | Ouyang ............... G01N 27/902 324/242 |

(Continued)

FOREIGN PATENT DOCUMENTS

| CN | 101303399 A | 11/2008 |
| CN | 102309325 A | 1/2012 |

(Continued)

OTHER PUBLICATIONS

ARMIN: "Making stuff: bend sensor", https://www.amphioxus.org/content/making-stuff-bend-sensor (posted on Jan. 2, 2011.).

(Continued)

*Primary Examiner* — Mohammad K Islam
(74) *Attorney, Agent, or Firm* — Lempia Summerfield Katz LLC

(57) ABSTRACT

A module for use in a magnetic resonance apparatus, a system, and a method for predicting a potential failure of a module are provided. The module includes at least one sensor configured to detect values of at least one module parameter of the module. The module parameter, such as detected values thereof, is suitable for predicting a potential failure of the module on the basis thereof.

16 Claims, 3 Drawing Sheets

(56) References Cited

U.S. PATENT DOCUMENTS

| | | | | |
|---|---|---|---|---|
| 9,002,431 | B2* | 4/2015 | Jones | G01R 33/34007 |
| | | | | 343/718 |
| 10,184,997 | B2* | 1/2019 | Piferi | G01R 33/34 |
| 10,267,875 | B2* | 4/2019 | Van Leeuwen | G01R 33/288 |
| 10,444,277 | B2* | 10/2019 | Van Wieringen | G06N 3/047 |
| 11,191,973 | B2* | 12/2021 | Escalona | A61M 60/873 |
| 11,903,715 | B1* | 2/2024 | Deka | A61B 5/245 |
| 2008/0278175 | A1 | 11/2008 | Wexler | |
| 2011/0245733 | A1 | 10/2011 | Goldbeck et al. | |
| 2012/0001635 | A1 | 1/2012 | Ookawa | |
| 2012/0200301 | A1* | 8/2012 | Ganesh | G01R 15/148 |
| | | | | 324/537 |
| 2014/0275973 | A1* | 9/2014 | Schuele | A61B 5/702 |
| | | | | 600/415 |
| 2015/0227838 | A1 | 8/2015 | Wang et al. | |
| 2015/0293188 | A1 | 10/2015 | Haider | |
| 2016/0327606 | A1 | 11/2016 | Van Wieringen | |
| 2017/0205478 | A1 | 7/2017 | Brinker | |
| 2017/0343626 | A1 | 11/2017 | Tomiha | |
| 2017/0367767 | A1* | 12/2017 | Blumenkranz | A61B 34/20 |
| 2019/0072624 | A1 | 3/2019 | Biber | |
| 2019/0154774 | A1* | 5/2019 | Hushek | A61B 5/055 |
| 2019/0304600 | A1 | 10/2019 | Mogatadakala | |
| 2019/0339337 | A1* | 11/2019 | Sharma | G01R 33/098 |
| 2019/0347177 | A1* | 11/2019 | Citirik | G01R 33/0385 |
| 2020/0185085 | A1 | 6/2020 | Mavrieudus et al. | |
| 2021/0293915 | A1 | 9/2021 | Fenchel et al. | |

FOREIGN PATENT DOCUMENTS

| | | |
|---|---|---|
| CN | 106506576 A | 3/2017 |
| EP | 2255727 A1 | 12/2010 |
| EP | 3882648 A1 | 9/2021 |
| JP | 2017213371 A | 12/2017 |
| KR | 20180050487 A | 5/2018 |

OTHER PUBLICATIONS

German Office Action for German Application No. 10 2020 207 363.5 dated May 5, 2021.

Jeong, Useok, and Kyu-Jin Cho. "A novel low-cost, large curvature bend sensor based on a Bowden-cable." Sensors 16.7 (2016): 961. pp. 1-20.

Kuhnert, Nadine, Lea Pflüger, and Andreas Maier. "Prediction of mri hardware failures based on image features using time series classification." Jan. 5, 2020. Springer Vieweg, Wiesbaden, 2020. 131-136.

Majeau, Lucas, et al. "Dataglove for consumer applications." 2011 7th International Workshop on Fibre and Optical Passive Components. IEEE, 2011.

Mehmann, Andreas, et al. "On the bending and stretching of liquid metal receive coils for magnetic resonance maging." IEEE Transactions on Biomedical Engineering 66.6 (2018): 1542-1548.

Wikipedia: PHOSFOS, https://en.wikipedia.org/wiki/PHOSFOS, researched on May 20, 2020. pp. 1-5.

Liu Long:"Research on Several Methods for Structural Damage Identification Based on Vibration Testing", p. 1-16, with English summary, Apr. 30, 2014.

Shen Chungen, et al:"UG NX 8.5 Finite Element Analysis and Case Study, 2nd edition", Machinery Industry Press, p. 1-18, with English summary, Mar. 31, 2015.

Zeng Chuanqing et al:"Sensing Technology and Engineering Applications", p. 25-29, with English abstract, Aug. 30, 2011.

* cited by examiner

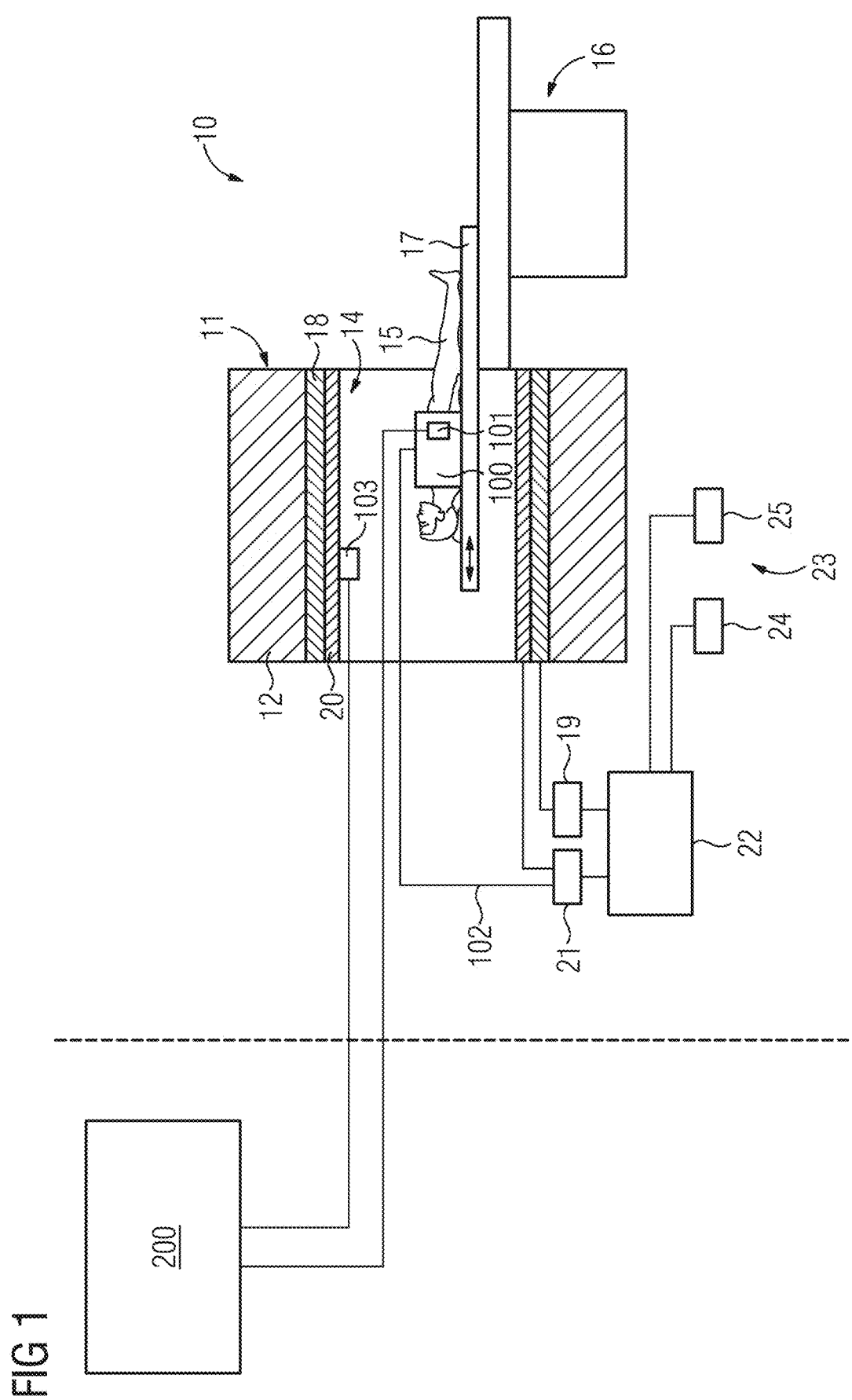

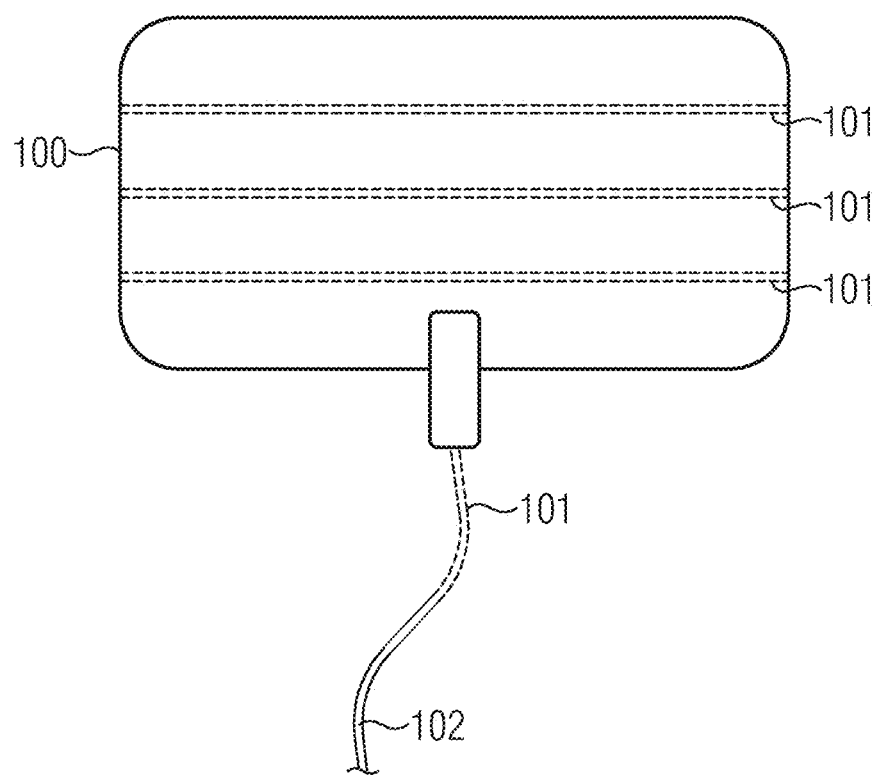
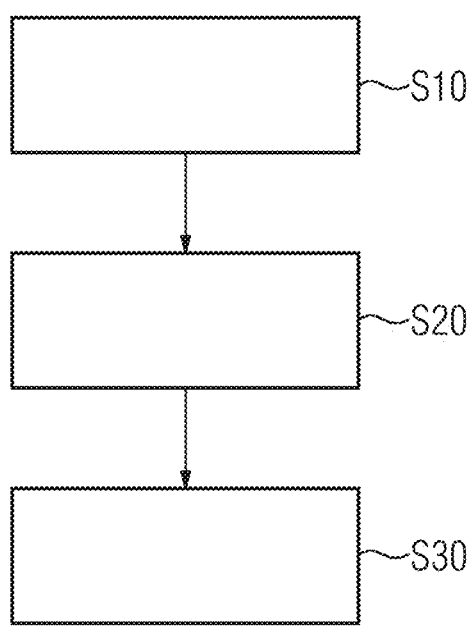

FIG 4

| Layer (type) | Output Shape | Param # |
| --- | --- | --- |
| lstm_1 (LSTM) | (None, 50, 100) | 50400 |
| dropout 1 (Dropout) | (None, 50, 100) | 0 |
| lstm_2 (LSTM) | (None, 50) | 30200 |
| dropout 2 (Dropout) | (None, 50) | 0 |
| dense 1 (Dense) | (None, 1) | 51 |

PREDICTING A POTENTIAL FAILURE OF A MODULE FOR USE IN A MAGNETIC RESONANCE APPARATUS

This application claims the benefit of German Patent Application No. DE 10 2020 207 363.5, filed on Jun. 15, 2020, which is hereby incorporated by reference in its entirety.

BACKGROUND

The present embodiments relate to a module for use in a magnetic resonance apparatus, a system, and a method for predicting a potential failure of a module.

Magnetic resonance tomography (MRT) or magnetic resonance imaging (MRI) is a known technology for generating images of an interior of the body of a patient. For this purpose, in a magnetic resonance apparatus, rapidly switched gradient pulses are typically overlaid onto a static basic magnetic field. Further, radiofrequency excitation signals are irradiated into the patient by a transmit coil. As a result of this, magnetic resonance signals are triggered. The magnetic resonance signals are received by magnetic resonance coils.

In order to record magnetic resonance signals with a high signal-to-noise ratio, the magnetic resonance signals being received may be brought as close as possible to the body of the patient. Local coils and/or surface coils that are placed on the body are particularly suitable as magnetic resonance coils. In order to be able to follow the contour of the body as effectively as possible, flexible magnetic resonance coils are often used, which may be adapted in an adjustable manner.

SUMMARY AND DESCRIPTION

The scope of the present invention is defined solely by the appended claims and is not affected to any degree by the statements within this summary.

Failure due to a defect in a magnetic resonance coil or also other units of the magnetic resonance apparatus may considerably disrupt the operation of the magnetic resonance apparatus. The present embodiments may obviate one or more of the drawbacks or limitations in the related art. For example, such disruptions may be avoided to the greatest possible extent.

A module for use in a magnetic resonance apparatus is provided. In this context, the module includes at least one sensor that is configured to detect values of at least one module parameter of the module. The module parameter (e.g., detected values thereof) is suitable for predicting a potential failure of the module on the basis thereof.

In one embodiment, the module includes an interface that is configured to transmit the detected values of the module parameter to an evaluation unit in order to predict a potential failure of the module based on the detected values.

In one embodiment, the at least one sensor is MR-compatible (e.g., is non-magnetic).

By predicting a potential failure, an impending failure may be identified at an early stage, and suitable measures may be initiated. For example, this makes it possible to replace the module before a failure of the module actually occurs.

For example, the module may include a flexible magnetic resonance coil, a cable, and/or a cooling line. For example, the cable may be a flexible cable. Flexible magnetic resonance coils and/or a flexible cable are especially at risk of a defect due to the mechanical stresses that act upon the flexible magnetic resonance coils and/or the flexible cable. For example, the flexible magnetic resonance coil may be a flexible local coil and/or surface coil. In one embodiment, on the basis of the detected module parameters of the flexible cable, it is possible to predict a potential broken cable at an early stage.

The flexible cable may be attached to a rigid magnetic resonance coil, for example. A rigid magnetic resonance coil may be a knee or wrist coil, for example.

For example, the cable may also be a supply cable of a gradient coil. Due to the high gradient currents in high magnetic fields, strong vibrations are often produced. These cables are therefore subjected to a particular strain, providing that it is particularly advantageous to predict a potential failure here.

In one embodiment, cooling lines (e.g., within a magnetic resonance apparatus, between a magnetic resonance apparatus and a device cabinet, and/or within the device cabinet) are monitored.

In one embodiment, the at least one module parameter describes a flexing and/or a temperature that act on the module.

In addition to mechanical stresses, thermal stresses may also occur, which may lead to a failure of the module. It is therefore advantageous to also detect thermal stresses.

In one embodiment, the at least one sensor includes at least one flex sensor, a photodiode (e.g., an infrared photodiode (IR photodiode)), a fiber-optic cable, a temperature sensor, a smoke sensor, a flow rate sensor, and/or a humidity sensor.

Flex sensors are particularly suitable for detecting module parameters that describe a flexing that acts upon the module. Temperature sensors are particularly suitable for detecting module parameters that describe a temperature that acts upon the module.

In one embodiment, the at least one flex sensor and/or the at least one temperature sensor are embedded in the module. For example, the at least one flex sensor is embedded in a planar and/or blanket-shaped layer (e.g., a foam material) of a flexible magnetic resonance coil.

The at least one flex sensor and/or the at least one temperature sensor may also be embedded in an insulating material of a flexible cable.

In one embodiment, flex sensors are installed in cables that are subjected to frequent flexing changes, such as speaker or ECG cables.

In one embodiment, installed flex sensors may additionally deliver information regarding the patient dimensions, which, for example, enables a more accurate SAR calculation or the targeted selection of coil elements or scan protocols adapted to the patient, and therefore an improved image reconstruction.

The temperature sensor may be integrated in a Hall effect sensor. The temperature sensor may be configured to detect the application of energy and/or heat into the module (e.g., to plot these over a longer period of time).

In one embodiment, the at least one sensor includes a combination of at least one photodiode (e.g., an IR photodiode) and at least one fiber-optic cable. For example, the at least one photodiode and the at least one fiber-optic cable are installed in the module such that the fiber-optic cable is also bent when flexing the module. In one embodiment, the photodiode is configured to measure an intensity of a light passing through the fiber-optic cable at a defined exit point of the fiber-optic cable. For example, arranged at one end of the fiber-optic cable is a light-emitting diode (LED) that couples light into the fiber-optic cable, and arranged at the other end of the fiber-optic cable is a photodiode that measures light that exits at this end.

The more strongly the fiber-optic cable is bent, the more strongly light that passes through the fiber-optic cable exits the fiber-optic cable at bend points. By bending the fiber-optic cable, the intensity of a light passing through the fiber-optic cable is therefore attenuated. The light exits at the defined exit point of the fiber-optic cable (e.g., at one end of the fiber-optic cable). The intensity of the light detected by the photodiode is therefore a measure for the bending of the module.

For example, this embodiment makes it possible for deformation of the module at individual points to be able to be disregarded, and for the overall deformation of the module to be detected instead. Further, a photodiode may be operated with simple electronics, and evaluation on the basis of the light intensity would also be simple. In one embodiment, when using an IR photodiode, it would also be possible to operate with thermal blankets, as IR radiation would be partially transmitted through thermal blankets and the IR photodiode would therefore also detect the light scattered by the thermal blanket.

With the aid of a flex sensor, a temperature sensor, a flow rate sensor, and/or a humidity sensor, it may be possible to observe the state of a cooling line.

Further, a system that includes a previously described module, an evaluation unit, and a transfer unit for transferring detected values of the at least one module parameter to the evaluation unit is provided. In this context, the evaluation unit is configured to predict a potential failure of the module based on the at least one module parameter.

The evaluation may include a memory (e.g., an electronic memory) and/or a computing unit (e.g., a programmable computing unit). The computing unit may include at least one processor.

In one embodiment, the evaluation unit is configured to receive values of module parameters from modules of various magnetic resonance apparatuses. For example, the evaluation unit is part of a central server. Various modules may send the values of corresponding module parameters to this server, so that the evaluation unit may draw on a large database. In one embodiment, this enables "big data analytics". The evaluation unit may be configured to link the values of the module parameters with further data in order to be able to make more accurate and/or more reliable predictions.

A further embodiment of the system provides that the system includes additional sensors outside of the at least one module for detecting the at least one module parameter. For example, one or more cameras are attached to the magnetic resonance apparatus, which are able to detect a deformation of the module.

For example, fiber-optic cables are arranged on the surface of the module. The module may further include light sources (e.g., light-emitting diodes (LEDs)) that couple light into the fiber-optic cables. Light components that decouple from the fiber-optic cables again may be detected by cameras arranged outside of the module. The flexing of the module may be inferred therefrom.

Further, a method for predicting a potential failure of a previously described module is provided.

The advantages of the method of the present embodiments for predicting a potential failure substantially correspond to the advantages of the module or the system, as described in detail above. Features, advantages, or alternative embodiments mentioned herein may likewise also be transferred to the other subject matter and vice versa.

In other words, the object may also be developed with the features disclosed or claimed in conjunction with a method. The corresponding functional features of the method are embodied by corresponding object-related units in this case.

The method for predicting a potential failure of a module includes detecting values of at least one module parameter of the module via at least one sensor of the module, analyzing the values of the at least one module parameter via an evaluation unit, and outputting a prediction value of a potential failure of the module.

The detected values may be electrical values, for example (e.g., electrical resistance values, electrical current values, and/or electrical voltage values).

On the basis of the output prediction value, it is possible to plan maintenance measures and/or service calls, for example.

The at least one module parameter may be transferred to an evaluation unit (e.g., via a remote data transfer). The evaluation unit may therefore be operated remote from the magnetic resonance apparatus with which the module is operated.

For example, the output may take place on an output unit, to which, for example, the operator and/or manufacturer of the magnetic resonance apparatus has access. The operator and/or the manufacturer may thus plan the availability and/or a necessary replacement of the module.

In one embodiment, each detected value of the at least one module parameter is assigned a time (e.g., the values are provided with a timestamp).

For example, detected electrical values are assigned the points in time at which the electrical values are detected. In one embodiment, it is possible, for example, to derive a temporal course of the electrical values. From the temporal course, for example, it is possible to identify a wear of the module (e.g., of a flexible cable).

In one embodiment, the analysis is performed by applying a model and/or a trained function to input data, where the input data is based on the at least one module parameter.

In one embodiment, the trained function has been trained (e.g., exclusively) on detected module parameters and points in time of failure of defective modules. The data that has accumulated in the past may be used to train the function.

In one embodiment, the trained function is based on a neural network (e.g., a long short-term memory (LSTM) or gated recurrent unit (GRU) network).

In one embodiment, the model and/or the trained function is dependent upon a number of connection procedures of the module to other parts of a magnetic resonance apparatus and/or a duration (e.g., a cumulative duration) of at least one flexing of the module and/or a degree (e.g., an average degree) of the flexing of the module and/or a change over time of a degree (e.g., an average degree) of the flexing of the module and/or a point in time of commissioning the module and/or an operating time of the module.

The connection procedures of the module to other parts of a magnetic resonance apparatus may include plug-in procedures of a magnetic resonance coil, for example. These may offer an indication of the wear of the magnetic resonance coil.

The duration and/or the degree of the deformation also represent further possible measures of the stress of the module. The point in time of commissioning the module, from which it is possible, for example, to derive the age of the module, and the operating time offer further indications of the wear of the module.

Further, a computer program product that includes a program and may be directly loaded into a memory of a programmable computing unit of the evaluation unit, and has program means (e.g., libraries and auxiliary functions) in order to carry out a method according to the present embodiments when the computer program product is executed in the computing unit is provided. In this context, the computer program product may include a piece of software with a source code that still has to be compiled and linked or is to only be interpreted, or an executable software code that, for execution, only is to be loaded into the computing unit. By way of the computer program product, the method according to the present embodiments may be carried out in a rapid, identically repeatable, and robust manner. The computer program product is configured such that the computer program product may carry out the method acts according to the present embodiments by the computing unit. In each case, the computing unit may have the requirements such as, for example, a corresponding RAM, a corresponding graphics card, or a corresponding logic unit in order to be able to carry out the respective method acts efficiently.

The computer program product is stored, for example, on a computer-readable medium (e.g., a non-transitory computer readable storage medium) or is deposited on a network or server from where the computer program product may be loaded into the processor of a local computing unit. In addition, control data of the computer program product may be stored on an electronically readable data carrier. Examples of electronically readable data carriers are a DVD, a magnetic tape, or a USB stick, on which electronically readable control information (e.g., software) is stored.

If this control information is read from the data carrier and stored in a system control unit of the magnetic resonance apparatus, all the embodiments according to the present embodiments of the above-described methods may be carried out. The present embodiments may therefore also proceed from the aforementioned computer-readable medium and/or the aforementioned electronically readable data carrier.

BRIEF DESCRIPTION OF THE DRAWINGS

Parts that correspond to one another are provided with the same reference characters in all the figures, in which:

FIG. 1 shows a schematic representation of one embodiment of a magnetic resonance apparatus;

FIG. 2 shows one embodiment of a magnetic resonance coil and a cable as modules for use in a magnetic resonance apparatus;

FIG. 3 shows a block diagram of one embodiment of a method for predicting a potential failure of a module; and FIG. 4 shows an overview of a possible LSTM network architecture for predicting a potential failure of a module.

DETAILED DESCRIPTION

FIG. 1 shows a schematic representation of one embodiment of a magnetic resonance apparatus 10. The magnetic resonance apparatus 10 includes a magnet unit 11 that has a main magnet 12 for generating a powerful main magnetic field that, for example, is constant over time. The magnetic resonance apparatus 10 also includes a patient receiving region 14 for accommodating a patient 15. In the present exemplary embodiment, the patient receiving region 14 is shaped as a cylinder and is enclosed in a circumferential direction cylindrically by the magnet unit 11. In principle, however, the patient receiving region 14 may have a different design. The patient 15 may be moved into the patient receiving region 14 by a patient positioning apparatus 16 of the magnetic resonance apparatus 10. For this purpose, the patient positioning apparatus 16 has a patient table 17 that is configured to be movable within the patient receiving region 14.

The magnet unit 11 further has a gradient coil unit 18 for generating magnetic field gradients that are used for spatial encoding during imaging. The gradient coil unit 18 is controlled by a gradient control unit 19 of the magnetic resonance apparatus 10. The magnet unit 11 furthermore includes a radiofrequency antenna unit 20 that, in the present exemplary embodiment, is configured as a body coil that is integrated in the magnetic resonance apparatus 10 in a fixed manner. The radiofrequency antenna unit 20 is configured to excite atomic nuclei. The excitation is established in the main magnetic field 13 generated by the main magnet 12. The radiofrequency antenna unit 20 is controlled by a radiofrequency antenna control unit 21 of the magnetic resonance apparatus 10 and radiates high-frequency magnetic resonance sequences into an examination space that is substantially formed by a patient receiving region 14 of the magnetic resonance apparatus 10. The radiofrequency antenna unit 20 is also configured to receive magnetic resonance signals.

The magnetic resonance apparatus 10 has a system control unit 22 for controlling the main magnet 12, the gradient control unit 19, and for controlling the radiofrequency antenna control unit 21. The system control unit 22 centrally controls the magnetic resonance apparatus 10 (e.g., performing a predetermined imaging gradient echo sequence). Additionally, the system control unit 22 includes an evaluation unit (not shown in detail) for evaluating medical image data that is detected during the magnetic resonance examination. In addition, the magnetic resonance apparatus 10 includes a user interface 23 that is connected to the system control unit 22. Control data such as imaging parameters, for example, and reconstructed magnetic resonance images may be displayed to medical operating personnel on a display unit 24 (e.g., on at least one monitor) of the user interface 23. Further, the user interface 23 has an input unit 25 that may be used by the medical operating personnel to enter information and/or parameters during a measurement process.

The magnetic resonance apparatus 10 is connected to a flexible magnetic resonance coil 100 via a flexible cable 102. The flexible cable 102 and the flexible magnetic resonance coil 100 are exemplary modules for use in the magnetic resonance apparatus 10. The magnetic resonance coil 100 includes a sensor 101 that is configured to detect values of at least one module parameter of the magnetic resonance coil 100. The module parameter is suitable for predicting a potential failure of the magnetic resonance coil 100 on the basis thereof.

The detected values may be transferred to an evaluation unit 200 via a transfer unit (e.g., via a remote data transfer). The evaluation unit is configured to predict a potential failure of the module based on the at least one module parameter.

In one embodiment, the evaluation unit 200 is configured to receive values of module parameters from modules of various magnetic resonance apparatuses (not shown in FIG. 1).

An additional sensor 103 is arranged outside of the flexible magnetic resonance coil 100 on the magnetic resonance apparatus 10. This sensor 103 (e.g., a camera) is also suitable for detecting at least one module parameter, such as the flexing, for example.

By way of example, FIG. 2 shows a flexible magnetic resonance coil 101 and a flexible cable 102 as modules for use in a magnetic resonance apparatus. Both the flexible magnetic resonance coil 101 and the flexible cable 102 include a plurality of flex sensors 102 that are configured to detect a flexing of the flexible magnetic resonance coil 101 and the flexible cable 102. The module parameter may therefore describe a flexing that acts upon the flexible magnetic resonance coil 101.

In one embodiment, the module parameter may also describe other properties, such as a temperature that acts upon the flexible magnetic resonance coil 101, for example. In this case, the module includes a temperature sensor.

FIG. 3 shows a schematic representation of one embodiment of a method for predicting a potential failure of a module, such as the flexible magnetic resonance coil or the flexible cable 102, for example. In act S10, values of at least one module parameter of the module are detected by way of at least one sensor of the module. In act S20, the at least one module parameter is analyzed by an evaluation unit. In act S30, a prediction value of a potential failure of the module is output.

The analysis in act S20 is performed, for example, by applying a model and/or a trained function to input data. The input data is based on the at least one module parameter.

In one embodiment, at least one parameter of the trained function is based on a comparison with module parameters that have been detected for other modules. For example, module parameters are detected for a large number of magnetic resonance coils 100 that may also be operated on various magnetic resonance apparatuses.

For example, the trained function may be trained on detected module parameters and points in time of failure of defective modules.

In this context, a neural network may be used (e.g., long short-term memory (LSTM) or gated recurrent unit (GRU)) network. FIG. 4 shows, on an exemplary basis, an overview of a possible LSTM network architecture for a given number of features. In this context, the input data has the following arrangement: input_shape=(sequence_length, nb_features).

The method described in detail above, the presented modules, and the magnetic resonance apparatus are merely exemplary embodiments that may be modified by a person skilled in the art in many ways without departing from the scope of the invention. Further, the use of the indefinite article "a" or "an" does not preclude the relevant features also being present plurally. Similarly, the expression "unit" does not exclude the relevant components consisting of a plurality of cooperating subcomponents that may also be spatially distributed if required.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A module for use in a magnetic resonance apparatus, the module comprising:
   a flexible surface coil of the magnetic resonance apparatus;
   at least one flex sensor configured to detect values of at least one parameter relating to the flexing that acts upon the module, the flex sensor embedded in a planar and/or blanket-shaped layer of the flexible surface coil of the magnetic resonance apparatus;
   wherein the at least one parameter is usable for predicting a potential failure of the flexible surface coil of the magnetic resonance apparatus on the basis thereof.

2. The module of claim 1, further comprising a cable, a cooling line, or a combination thereof.

3. The module of claim 1, further comprising a temperature sensor embedded in the planar and/or blanket-shaped layer of the flexible surface coil of the magnetic resonance apparatus, the temperature sensor configured to detect values relating to relating to the heat that acts upon the module.

4. A system comprising:
   a module for use in a magnetic resonance apparatus, the module comprising at least one flex sensor configured to detect values of at least one module parameter of the module relating to the flexing that acts upon the module, the at least one flex sensor embedded in a planar and/or blanket-shaped layer of the module, wherein the at least one module parameter is usable for predicting a potential failure of the module on the basis thereof, wherein the module is a flexible surface coil;
   an evaluation unit;
   a transfer unit configured to transfer the detected values of the at least one module parameter to the evaluation unit, and
   wherein the evaluation unit is configured to predict a potential failure of the module based on the at least one module parameter.

5. The system of claim 4, wherein the evaluation unit is configured to receive values of module parameters from modules of various magnetic resonance apparatuses.

6. The system of claim 4, further comprising at least one additional sensor outside of the at least one module for detecting the at least one module parameter.

7. A method for predicting a possible failure of a module, the method comprising:
   detecting, by at least one flex sensor of the module, values of at least one module parameter of the module relating to a flexing that acts on the module;
   analyzing, by an evaluation unit, the at least one module parameter; and
   outputting a prediction value of a potential failure of the module,
   wherein the module is a flexible magnetic resonance coil, the flexible magnetic resonance coil being a flexible surface coil, wherein the at least one flex sensor is embedded in a planar and/or blanket-shaped layer of the flexible surface coil.

8. The method of claim 7, wherein the analyzing comprises applying a model, a trained function, or the model and the trained function to input data,
   wherein the input data is based on the at least one module parameter.

9. The method of claim 8, wherein the analyzing comprises applying the trained function to the input data, wherein at least one parameter of the trained function is based on a comparison with module parameters that have been detected for other modules.

10. The method of claim 8, wherein the trained function has been trained on detected module parameters and points in time of failure of defective modules.

11. The method of claim 10, wherein the trained function has been trained exclusively on the detected module parameters and the points in time of failure of the defective modules.

12. The method of claim 8, wherein the trained function is based on a neural network.

13. The method of claim 12, wherein the neural network is a long short-term memory (LSTM) or gated recurrent unit (GRU) network.

14. The method of claim 8, wherein the model, the trained function, or the model and the trained function are independent of:
- a number of connection procedures of the module to other parts of a magnetic resonance apparatus;
- a duration of at least one flexing of the module;
- a degree of the flexing of the module;
- a change over time of a degree of the flexing of the module;
- a point in time of commissioning the module;
- an operating time of the module; or
- any combination thereof.

15. The method of claim 14, wherein the model, the trained function, or the model and the trained function are independent of the duration of the at least one flexing of the module, the duration being a cumulative duration.

16. In a non-transitory computer-readable storage medium that stores instructions executable by an evaluation unit to predict a possible failure of a module, the instructions comprising:
- detecting, by at least one flex sensor of the module embedded in a planar and/or blanket-shaped layer of the flexible surface coil of the magnetic resonance apparatus, values of at least one module parameter of the module;
- analyzing the at least one module parameter; and
- outputting a prediction value of a potential failure of the module,
- wherein the module is a flexible magnetic resonance coil, the flexible magnetic resonance coil being a flexible surface coil,
- wherein the at least one module parameter describes a flexing that acts on the module.

* * * * *